US011384054B2

(12) United States Patent
Huang et al.

(10) Patent No.: US 11,384,054 B2
(45) Date of Patent: Jul. 12, 2022

(54) CRYSTALLINE FORM OF IVACAFTOR AND A PROCESS FOR PREPARING THE SAME

(71) Applicant: ScinoPharm Taiwan, Ltd., Tainan (TW)

(72) Inventors: Kuan-Hsun Huang, Tainan (TW); Li-Ting Wang, Tainan (TW); Inze Lin, Tainan (TW); Tsung-Cheng Hu, Tainan (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 0 days.

(21) Appl. No.: 17/200,132

(22) Filed: Mar. 12, 2021

(65) Prior Publication Data
US 2022/0127234 A1    Apr. 28, 2022

Related U.S. Application Data (60) Provisional application No. 63/104,274, filed on Oct. 22, 2020.

(51) Int. Cl.
*C07D 215/56*    (2006.01)

(52) U.S. Cl.
CPC ........ *C07D 215/56* (2013.01); *C07B 2200/13* (2013.01)

(58) Field of Classification Search
CPC .................. C07D 215/56; C07B 2200/13
See application file for complete search history.

(56) References Cited

U.S. PATENT DOCUMENTS

| 8,410,274 B2 * | 4/2013 | Hurter ................. A61P 25/16 546/159 |
| 8,471,029 B2 | 6/2013 | Arekar et al. |
| 9,809,551 B2 | 11/2017 | Akbarali et al. |
| 9,957,234 B2 | 5/2018 | Thaimattam et al. |

FOREIGN PATENT DOCUMENTS

| CN | 104725314 A | 6/2015 |
| WO | WO-2008104512 A2 | 9/2008 |
| WO | WO-2009038683 A2 | 3/2009 |
| WO | WO-2013158121 A1 | 10/2013 |
| WO | WO-2014118805 A1 | 8/2014 |
| WO | WO-2015128882 A2 | 9/2015 |
| WO | WO-2016057730 A1 | 4/2016 |
| WO | WO-2016092561 A2 | 6/2016 |
| WO | WO-2016199085 A1 | 12/2016 |
| WO | WO-2017118915 A1 | 7/2017 |

OTHER PUBLICATIONS

Korean Intellectual Property Office, International Search Report for International Application No. PCT/SG2021/050167 dated Jul. 19, 2021, 5 pages.
Korean Intellectual Property Office, Written Opinion for International Application No. PCT/SG2021/050167 dated Jul. 19, 2021, 6 pages.

\* cited by examiner

*Primary Examiner* — Timothy R Rozof
(74) *Attorney, Agent, or Firm* — Mintz, Levin, Cohn, Ferris, Glovsky and Popeo, P.C.

(57) ABSTRACT

In certain aspects, the invention provides crystalline forms of ivacaftor N-(2,4-di-tert-butyl-phenyl-5-hydroxy-phenyl)-1,4-dihydro-4-oxoquinoline-3-carboxamide. In related aspects, the invention provides a process for preparing any one of crystalline forms S2, S3, S4 and S5 of ivacaftor. The process includes: forming a solution including crude ivacaftor and a solvent; adding an anti-solvent to the solution to form slurry including a precipitate; isolating the precipitate; and drying the precipitate to provide crystalline form S2, S3, S4, or S5 of ivacaftor.

20 Claims, 8 Drawing Sheets

CRYSTALLINE FORM OF IVACAFTOR AND A PROCESS FOR PREPARING THE SAME

CROSS-REFERENCES TO RELATED APPLICATIONS

This application claims the benefit of priority to U.S. Provisional Application Ser. No. 63/104,274 filed Oct. 22, 2020, the entirety of which is incorporated herein by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Ivacaftor refers to N-(2,4-di-tert-butyl-phenyl-5-hydroxyphenyl)-1,4-dihydro-4-oxoquinoline-3-carboxamide having the structure:

Ivacaftor, also known as Kalydeco or VX-770, is a drug used for the treatment of cystic fibrosis, which acts as a potentiator at the cystic fibrosis transmembrane conductance regulator (CFTR) channel to improve its activity. Ivacaftor has been approved by the U.S. Food and Drug Administration for the treatment of cystic fibrosis in patients aged 2 years and older who have a mutation in the CFTR gene.

U.S. Pat. No. 8,410,274 discloses solid forms of ivacaftor, including crystalline form A, crystalline form B, and an amorphous form and the preparation thereof. Specifically, crystalline form A of ivacaftor was prepared by heating ivacaftor as a solid to a temperature of at or above its melting point, for example to about 250° C. and then cooling to room temperature. Crystalline form B of ivacaftor was prepared by heating a slurry of ivacaftor in refluxing acetonitrile for 24 hours, and then cooling the mixture to about room temperature, e.g., about 20° C. Amorphous ivacaftor was obtained from a crystalline form of ivacaftor, for example crystalline form A or crystalline form B. Accordingly, a substantially amorphous form of ivacaftor was prepared by dissolving crystalline form B of ivacaftor into a solution and spray drying the solution. However, the preparation of crystalline forms A and B of ivacaftor has deficiencies. For example, an elevated temperature (212-215° C.) is required for the production of crystalline form A, which may result in a greater risk of ivacaftor degradation. In addition, the method requires high energy consumption, which may not be suitable for large scale manufacturing. As to crystalline form B, the crystallization takes a long period of time, therefore lacks efficiency. Further, crystalline form B was prepared by using a highly toxic solvent (i.e., acetonitrile) in the crystallization process.

U.S. Pat. No. 8,471,029 discloses crystalline form C of ivacaftor and its preparation. The crystalline form C was prepared by adding an excess of ivacaftor into acetonitrile and stirring at 90° C. for 3 days, and then cooling to room temperature. Similar to the preparation of crystalline form B as stated above, the preparation of crystalline form C of ivacaftor has shortcomings in the crystallization process, for example using a highly toxic solvent (i.e., acetonitrile) and is also time-consuming.

U.S. Pat. No. 9,809,551 B2 discloses crystalline form APO-I of Ivacaftor and MIBK (i.e., methyl isobutyl ketone) solvate. Form APO-I of Ivacaftor was prepared by the process including: (a) adding an ivacaftor solvate to an organic solvent or a mixture of organic solvents (e.g., methanol, ethanol, propanol, isopropanol, butanol, toluene, xylene, hexane, heptane or a mixture thereof), thereby forming a reaction mixture; (b) maintaining the reaction mixture at a temperature range of from about 0° C. to about 60° C.; and (c) isolating the polymorphic form APO-I of ivacaftor. As disclosed, the ivacaftor solvate can be a solvate of methanol, ethanol, methyl ethyl ketone, isopropyl acetate, acetonitrile, methyl isobutyl ketone or water.

CN Publication No. 104,725,314 discloses a crystalline form D prepared by crystallization of ivacaftor from a mixed solution of acetonitrile and water.

U.S. Pat. No. 9,957,234 discloses crystalline forms L1-L14 of ivacaftor and the preparation thereof.

PCT Publication Nos. 2009/038683, 2013/158121, 2014/118805, 2015/128882 and 2016/057730 disclose various crystalline forms of ivacaftor, including salts, solvates, co-crystals, or hydrates and the preparation thereof.

Although the above-mentioned crystalline forms have been disclosed, new solid forms of ivacaftor are still needed for enhancing the efficacy of ivacaftor in the treatment of cancers, as well as for improving the processes of preparing them. In particular, new solid forms of ivacaftor are needed in the manufacture of pharmaceutical formulations. The present invention meets this need, providing a novel crystalline form of ivacaftor and a process for preparing the crystalline form.

BRIEF SUMMARY OF THE INVENTION

In some aspects, the invention provides crystalline forms S2, S3, S4, and S5 of ivacaftor, each of which is characterized by the X-ray powder diffraction data, thermogravimetric analytical data, differential scanning calorimetry data and dynamic vapor sorption data described herein.

In another aspect, the invention provides a process for preparing any one of crystalline forms S2, S3, S4 and S5 of ivacaftor. The process includes: forming a solution containing crude ivacaftor and a solvent; adding an anti-solvent to the solution to form slurry containing a precipitate; isolating the precipitate; and drying the precipitate to provide crystalline form S2, S3, S4, or S5 of ivacaftor.

DETAILED DESCRIPTION OF THE INVENTION

I. General

The present invention provides four novel crystalline forms of ivacaftor having characteristics of exceptional crystallinity and stability. Among other advantages, the novel crystalline forms are prepared in high yield under mild conditions by using more environmentally friendly solvents during crystallization. Furthermore, the novel crystalline forms exhibit good stability and can be stored and/or used for the manufacture of medicaments. In particular, the novel crystalline forms can be directly used in pharmaceutical development without converting to other forms such as non-crystalline forms.

II. Definitions

"Crude" refers to a mixture including a desired compound (e.g., ivacaftor) and at least one other species (e.g., a solvent, a reagent such as an acid or a base, a starting material, or a byproduct of a reaction giving rise to the desired compound).

"Solvent" refers to a liquid substance capable of dissolving ivacaftor at about 50° C. to about 60° C. The term "anti-solvent" refers to a liquid substance which is not capable of dissolving ivacaftor at about 20° C. to about 30° C. More particularly, solvents and anti-solvents suitable for crystalline forms of ivacaftor are selected by solubility test, such as the Tables 1A, 2B, and 1C below, taking into consideration of advantages provided by the convenience and efficiency of process operation, the use of more environmentally friendly solvents, mild crystallization conditions, and others.

TABLE 1A

Solubility of ivacaftor in solvents at 25° C.

| Solvent | Acetone | Acetonitrile | Ethanol | Methanol | Isopropanol |
|---|---|---|---|---|---|
| Solubility (mg/mL) | 27.87 | 1.78 | 4.50 | 1.98 | 2.87 |

| Solvent | Ethyl acetate | n-Heptane | Cyclohexane | Tetrahydrofuran | Methyl ethyl ketone |
|---|---|---|---|---|---|
| Solubility (mg/mL) | 16.91 | 0.62 | 0.34 | 26.55 | 44.71 |

| Solvent | Water | Dimethyl sulfoxide | N,N-dimethylformamide |
|---|---|---|---|
| Solubility (mg/mL) | 0.00 | 374.81 | 108.76 |

TABLE 1B

Solubility of ivacaftor in acetone/water at 25° C.

| Solvent | mg/mL |
|---|---|
| 0% water in acetone | 27.87 |
| 2% water in acetone | 27.88 |
| 5% water in acetone | 41.41 |
| 10% water in acetone | 47.07 |
| 15% water in acetone | 43.26 |
| 30% water in acetone | 11.00 |
| 50% water in acetone | 0.34 |

TABLE 1C

Solubility of ivacaftor in acetone/water at 25° C.

| Solvent | mg/mL |
|---|---|
| 8% water in acetone | 41.2 |

"Cooling" refers to the process of reducing the temperature of a substance or mixture of substances.

"Heating" refers to the process of increasing the temperature of a substance or mixture of substances.

"Precipitating" refers to the process of causing a compound in a solution to coalesce into a solid form of the substance (i.e., a precipitate). The entirety of a compound in a solution, or any fraction thereof, can be caused to precipitate. The solid form of the substance can be amorphous or crystalline.

"Crystalline form" refers to a solid form of a compound wherein the constituent molecules are packed in a regularly ordered, repeating pattern. A crystalline form can include triclinic, monoclinic, orthorhombic, tetragonal, trigonal, hexagonal, and cubic crystal geometries. A crystalline form can include one or more regions, i.e., grains, with distinct crystal boundaries. A crystalline solid can include two or more crystal geometries.

"Amorphous form" refers to a solid form of a compound having no definite crystal structure, i.e., lacking a regularly ordered, repeating pattern of constituent molecules.

"Isolating" refers to the process of isolating at least a portion of a first substance (e.g., a precipitate) from a mixture including the substance and at least one additional substance. In some instances, the isolated substance is substantially free at least one of the additional substances present in the original mixture.

"Drying" refers to the removal of a liquid, such as a solvent, from a substance. Drying is frequently conducted by heating the substance, reducing the pressure under which the substance is stored, or both.

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

III. Crystalline Form S2 of Ivacaftor

Figure 1:
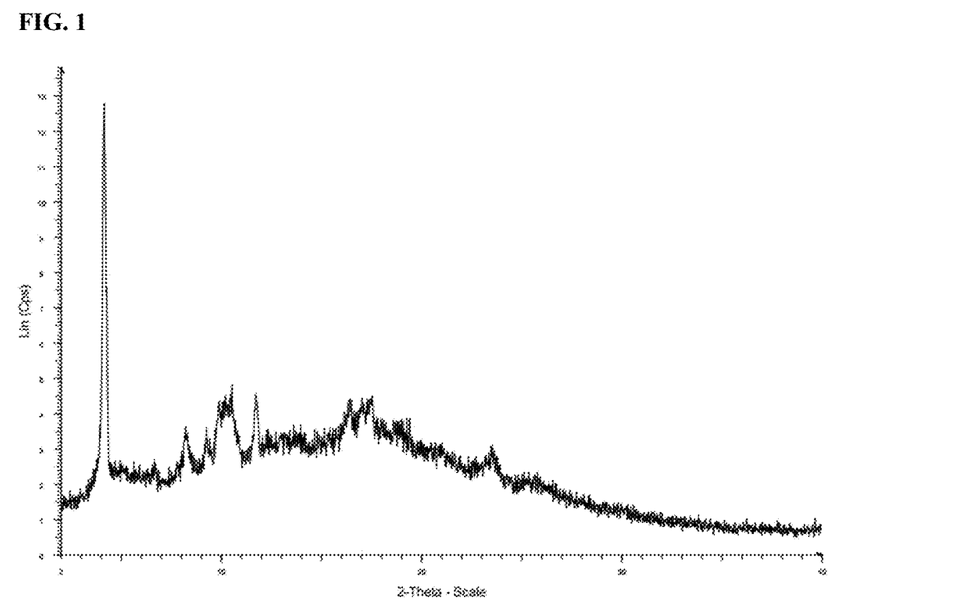
FIG. 1 shows the X-ray powder diffraction (XRPD) pattern recorded for crystalline form S2 of ivacaftor.

In a first aspect, the invention provides a crystalline form S2 of ivacaftor. In some embodiments, crystalline form S2 of ivacaftor is characterized by an X-ray powder diffraction pattern including one or more peaks (i.e., 1, 2, 3, 4, 5, 6, 7 or 8 peaks) at 4.1, 8.2, 9.3, 9.9, 10.4, 11.7, 16.4 and 17.4 degrees 2θ (±0.2 degrees 2θ). In some embodiments, crystalline form S2 of ivacaftor is characterized by an X-ray powder diffraction pattern including three or more peaks (i.e., 3, 4, 5, 6, 7 or 8 peaks) at 4.1, 8.2, 9.3, 9.9, 10.4, 11.7, 16.4 and 17.4 degrees 2θ (±0.2 degrees 2θ). In some embodiments, crystalline form S2 of ivacaftor is characterized by an X-ray powder diffraction pattern including five or more peaks (i.e., 5, 6, 7 or 8 peaks) at 4.1, 8.2, 9.3, 9.9, 10.4, 11.7, 16.4 and 17.4 degrees 2θ (±0.2 degrees 2θ). In some embodiments, crystalline form S2 of ivacaftor is characterized by an X-ray powder diffraction pattern including peaks at 4.1, 8.2, 9.3, 9.9, 10.4, 11.7, 16.4 and 17.4 degrees 2θ (±0.2 degrees 2θ). In some embodiments, crystalline form S2 of ivacaftor is characterized by an X-ray powder diffraction substantially in accordance with FIG. 1.

Methods for collection of XRPD data are known in the art, and any such methods can be used for characterizing the crystalline forms of ivacaftor. For example, the X-ray powder diffraction patterns described herein can be generated using Cu Kα1 radiation.

Figure 2:
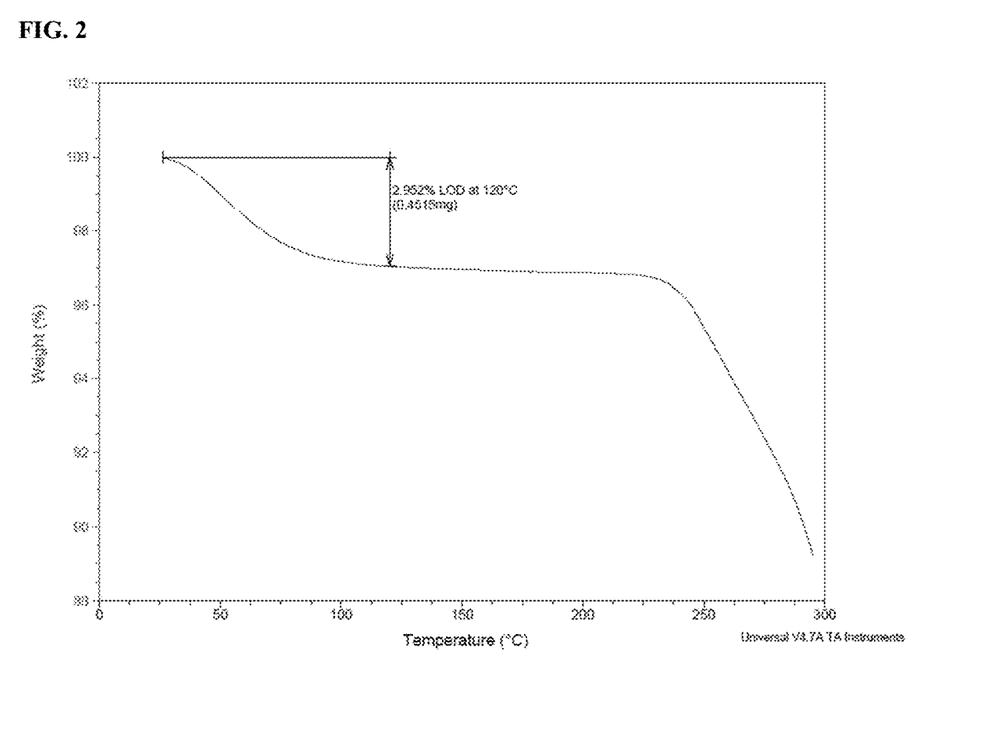
FIG. 2 shows the thermogravimetric analysis (TGA) thermogram recorded for crystalline form S2 of ivacaftor

In some embodiments, crystalline form S2 of ivacaftor is characterized by a weight loss of about 3% upon heating at about 120° C., as measured by a thermal gravimetric analysis. In some embodiments, the thermal gravimetric analysis is substantially in accordance with FIG. 2. In some such embodiments, the weight loss is measured using a sample weighing about 15-20 mg, which is subjected to a temperature of from 30° C. to 300° C. using a ramp of 10° C./min.

Figure 3:
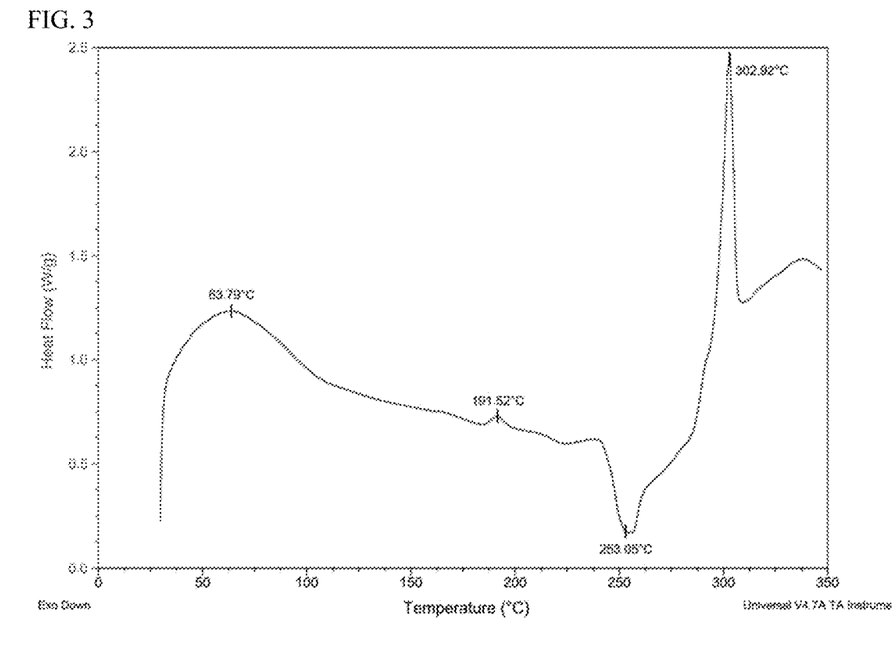
FIG. 3 shows the differential scanning calorimetry (DSC) thermogram recorded for crystalline form S2 of ivacaftor

In some embodiments, crystalline form S2 of ivacaftor is characterized by a differential scanning calorimetry thermogram including an endothermic peak at about 303° C. In some embodiments, crystalline form S2 of ivacaftor is characterized by a differential scanning calorimetry thermogram including three endothermic peaks at about 64° C., 192° C., and 303° C.; and one exothermic peak at about 253° C. In some embodiments, crystalline form S2 of ivacaftor is characterized by a differential scanning calorimetry thermogram substantially in accordance with FIG. 3. In some embodiments, a thermogram is recorded using a sample weighing about 1-5 mg, which is subjected to a temperature of from about 30° C. to 350° C. using a ramp of 10° C./min.

Figure 4:
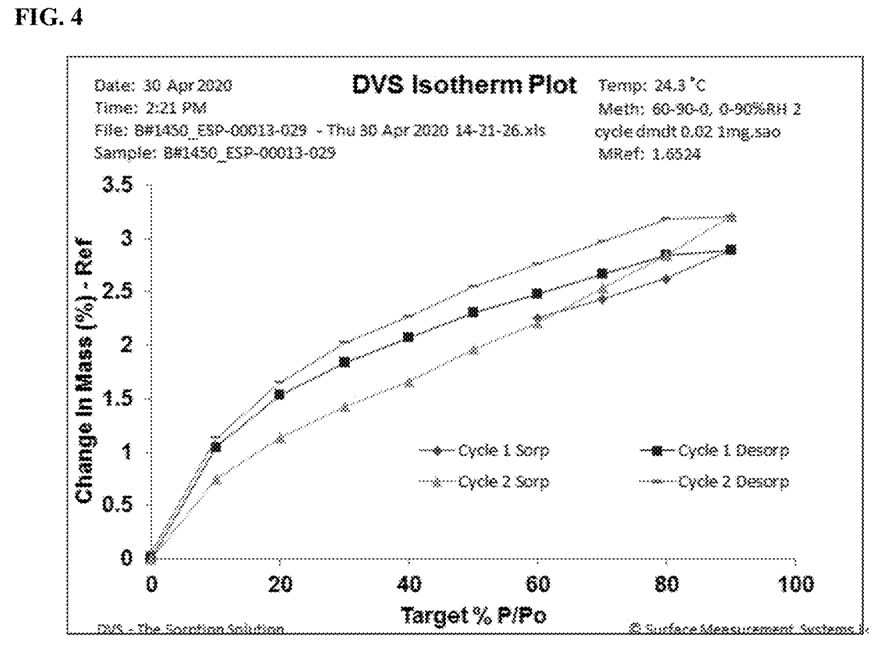
FIG. 4 shows the dynamic vapor sorption (DVS) measurement chart recorded for crystalline form S2 of ivacaftor.

In some embodiments, crystalline form S2 of ivacaftor is characterized by a dynamic vapor sorption (DVS) measurement chart substantially in accordance with FIG. 4.

IV. Crystalline Form S4 of Ivacaftor

Figure 9:
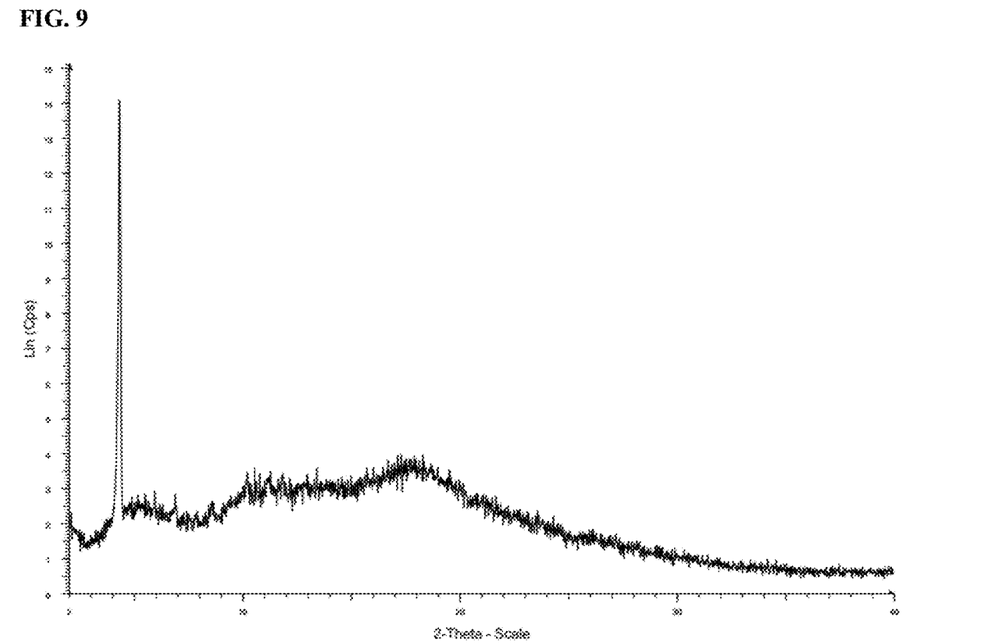
FIG. 9 shows the X-ray powder diffraction (XRPD) pattern recorded for crystalline form S4 of ivacaftor.

In a second aspect, the invention provides a crystalline form S4 of ivacaftor. In some embodiments, crystalline form S4 of ivacaftor is characterized by an X-ray powder diffraction pattern including one peak at 4.3 degrees 2θ (±0.2 degrees 2θ). In some embodiments, crystalline form S4 of ivacaftor is characterized by an X-ray powder diffraction substantially in accordance with FIG. 9.

Methods for collection of XRPD data are known in the art, and any such methods can be used for characterizing the crystalline forms of ivacaftor. For example, the X-ray powder diffraction patterns described herein can be generated using Cu Kα1 radiation.

Figure 10:
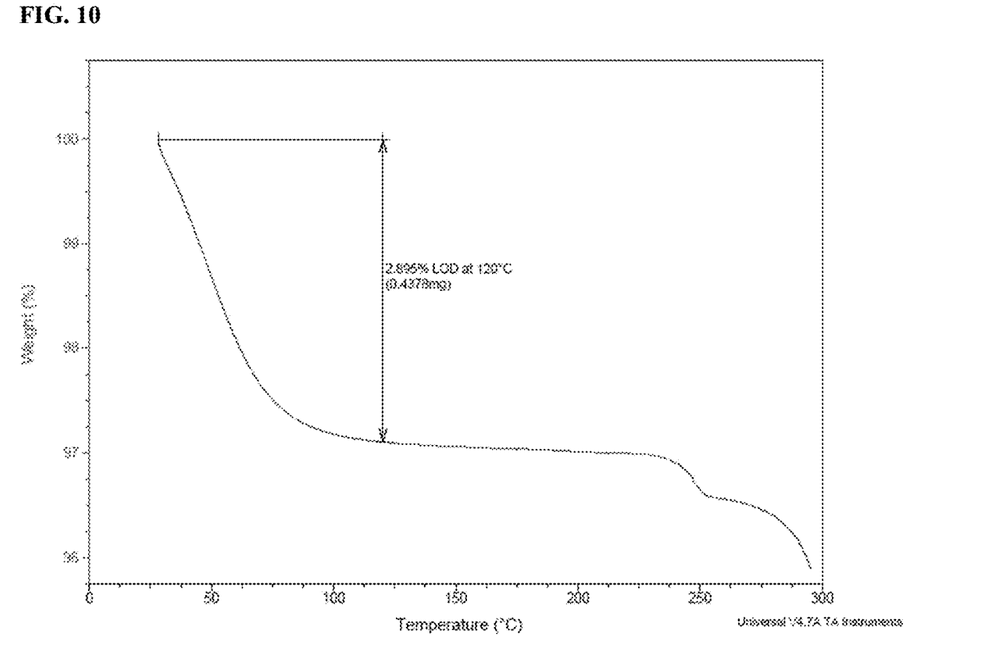
FIG. 10 shows the thermogravimetric analysis (TGA) thermogram recorded for crystalline form S4 of ivacaftor

In some embodiments, crystalline form S4 of ivacaftor is characterized by a weight loss of about 3% upon heating at about 120° C., as measured by thermal gravimetric analysis. In some embodiments, the thermal gravimetric analysis is substantially in accordance with FIG. 10. In some such embodiments, the weight loss is measured using a sample weighing about 15-20 mg, which is subjected to a temperature of from 30° C. to 300° C. using a ramp of 10° C./min.

Figure 11:
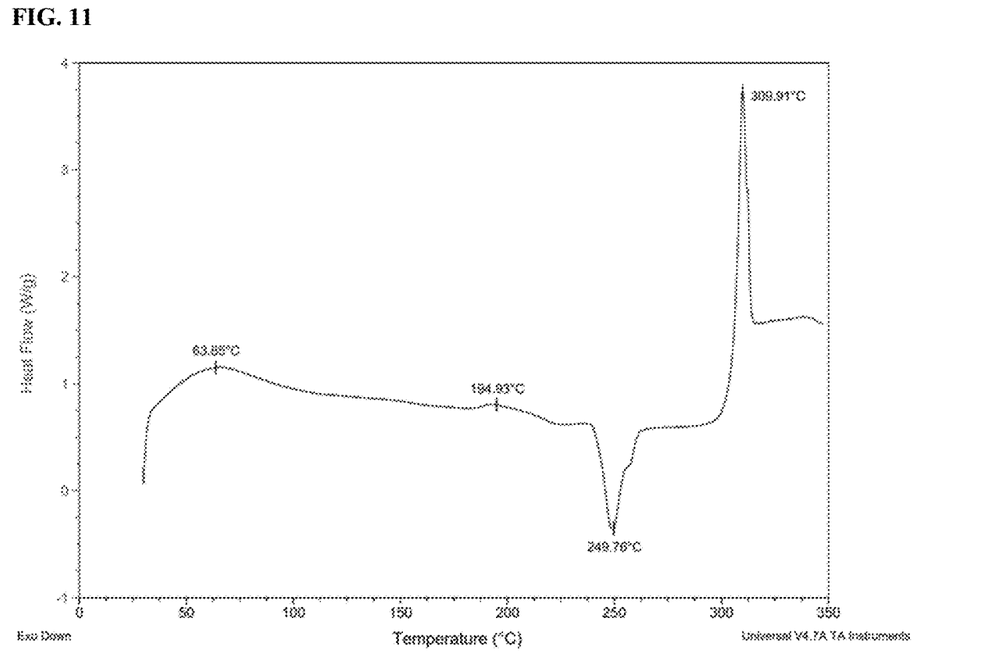
FIG. 11 shows the differential scanning calorimetry (DSC) thermogram recorded for crystalline form S4 of ivacaftor

In some embodiments, crystalline form S4 of ivacaftor is characterized by a differential scanning calorimetry thermogram including an endothermic peak at about 310° C. In some embodiments, crystalline form S4 of ivacaftor is characterized by a differential scanning calorimetry thermogram including three endothermic peaks at about 64° C., 195° C., and 309° C.; and one exothermic peak at about 250° C. In some embodiments, crystalline form S4 of ivacaftor is characterized by a differential scanning calorimetry thermogram substantially in accordance with FIG. 11. In some embodiments, a thermogram is recorded using a sample weighing about 1-5 mg, which is subjected to a temperature of from about 30° C. to 350° C. using a ramp of 10° C./min.

Figure 12:
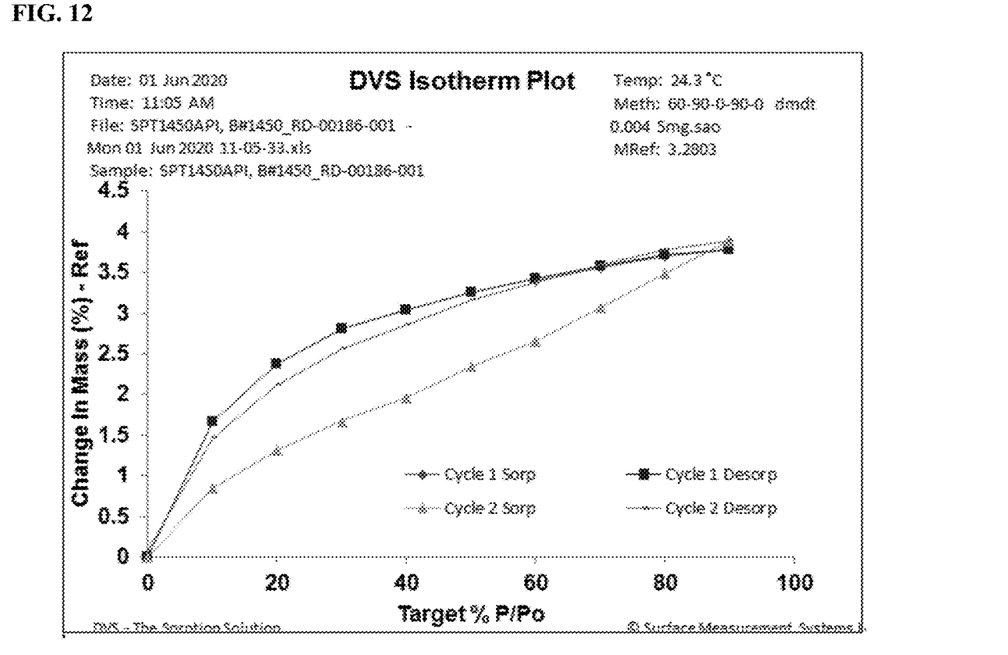
FIG. 12 shows the dynamic vapor sorption (DVS) measurement chart recorded for crystalline form S4 of ivacaftor.

In some embodiments, crystalline form S4 of ivacaftor is characterized by a dynamic vapor sorption (DVS) measurement chart substantially in accordance with FIG. 12.

V. Crystalline Form S5 of Ivacaftor

Figure 13:
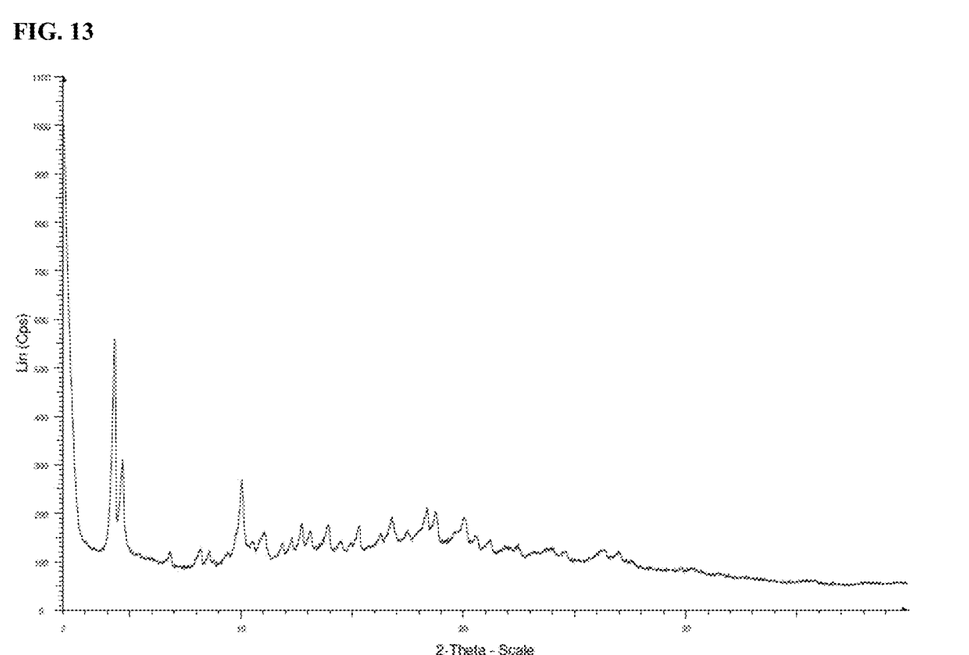
FIG. 13 shows the X-ray powder diffraction (XRPD) pattern recorded for crystalline form S5 of ivacaftor.

In a third aspect, the invention provides a crystalline form S5 of ivacaftor. In some embodiments, crystalline form S5 of ivacaftor is characterized by an X-ray powder diffraction pattern including one or more peaks (i.e., 1, 2, 3, 4, 5, 6, 7, 8, 9, or 10 peaks) at 4.3, 4.6, 10.0, 12.7, 13.9, 15.3, 16.8, 18.3, 18.8, and 20.0 degrees 2θ (±0.2 degrees 2θ). In some embodiments, crystalline form S5 of ivacaftor is characterized by an X-ray powder diffraction pattern including three or more peaks (i.e., 3, 4, 5, 6, 7, 8, 9, or 10 peaks) at 4.3, 4.6, 10.0, 12.7, 13.9, 15.3, 16.8, 18.3, 18.8, and 20.0 degrees 2θ (±0.2 degrees 2θ). In some embodiments, crystalline form S5 of ivacaftor is characterized by an X-ray powder diffraction pattern including five or more peaks (i.e., 5, 6, 7, 8, 9, or 10 peaks) at 4.3, 4.6, 10.0, 12.7, 13.9, 15.3, 16.8, 18.3, 18.8, and 20.0 degrees 2θ (±0.2 degrees 2θ). In some embodiments, crystalline form S5 of ivacaftor is characterized by an X-ray powder diffraction pattern including one or more peaks (i.e., 1, 2, 3, 4, or 5 peaks) at 4.3, 4.6, 10.0, 18.3 and 18.8 degrees 2θ (±0.2 degrees 2θ). In some embodiments, crystalline form S5 of ivacaftor is characterized by an X-ray powder diffraction pattern including peaks at 4.3, 4.6, 10.0, 18.3 and 18.8 degrees 2θ (±0.2 degrees 2θ). In some embodiments, crystalline form S5 of ivacaftor is characterized by an X-ray powder diffraction substantially in accordance with FIG. 13.

Methods for collection of XRPD data are known in the art, and any such methods can be used for characterizing the crystalline forms of ivacaftor. For example, the X-ray powder diffraction patterns described herein can be generated using Cu Kα1 radiation.

Figure 14:
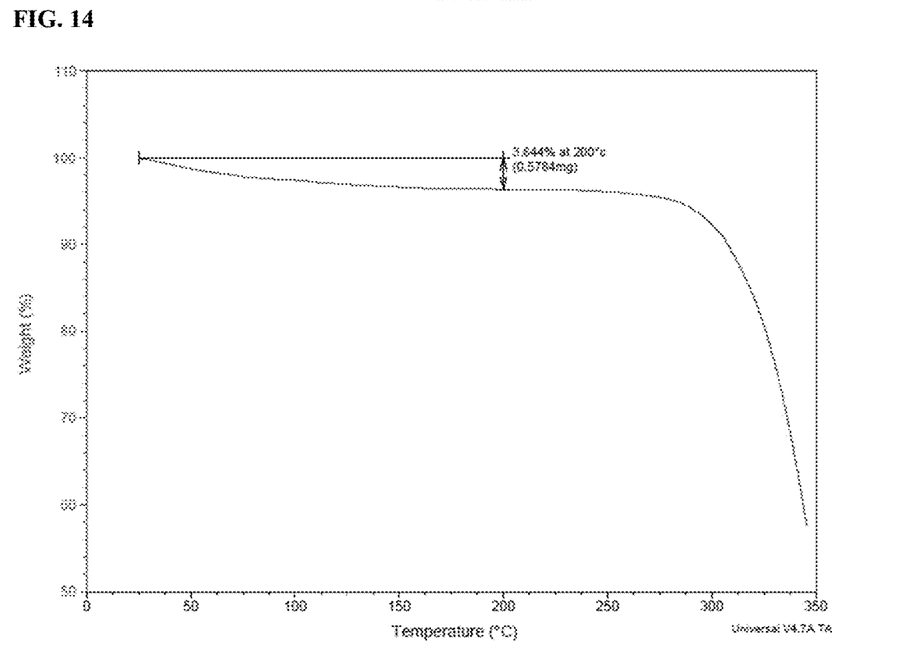
FIG. 14 shows the thermogravimetric analysis (TGA) thermogram recorded for crystalline form S5 of ivacaftor

In some embodiments, crystalline form S5 of ivacaftor is characterized by a weight loss of from about 3% to about 4% upon heating at about 200° C., as measured by thermal gravimetric analysis. In some embodiments, the thermal gravimetric analysis is substantially in accordance with FIG. 14. In some such embodiments, the weight loss is measured using a sample weighing about 15-20 mg, which is subjected to a temperature of from 30° C. to 300° C. using a ramp of 10° C./min.

Figure 15:
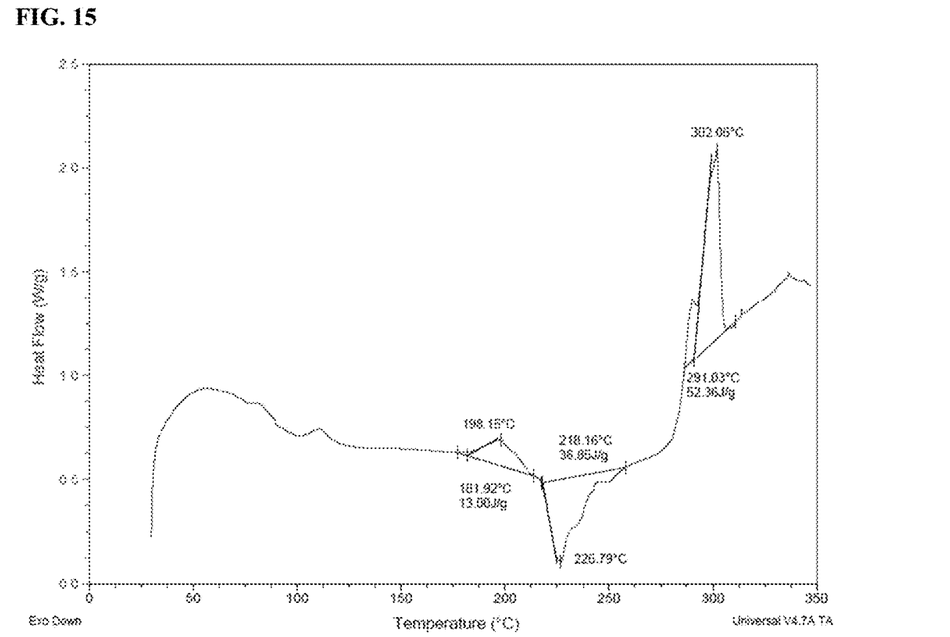
FIG. 15 shows the differential scanning calorimetry (DSC) thermogram recorded for crystalline form S5 of ivacaftor

In some embodiments, crystalline form S5 of ivacaftor is characterized by a differential scanning calorimetry thermogram including an endothermic peak at about 302° C. In some embodiments, crystalline form S5 of ivacaftor is characterized by a differential scanning calorimetry thermogram including three endothermic peaks at about 198° C. and 302° C.; and one exothermic peak at about 226° C. In some embodiments, crystalline form S5 of ivacaftor is characterized by a differential scanning calorimetry thermogram substantially in accordance with FIG. 15. In some embodiments, a thermogram is recorded using a sample weighing about 1-5 mg, which is subjected to a temperature of from about 30° C. to 350° C. using a ramp of 10° C./min.

Figure 16:
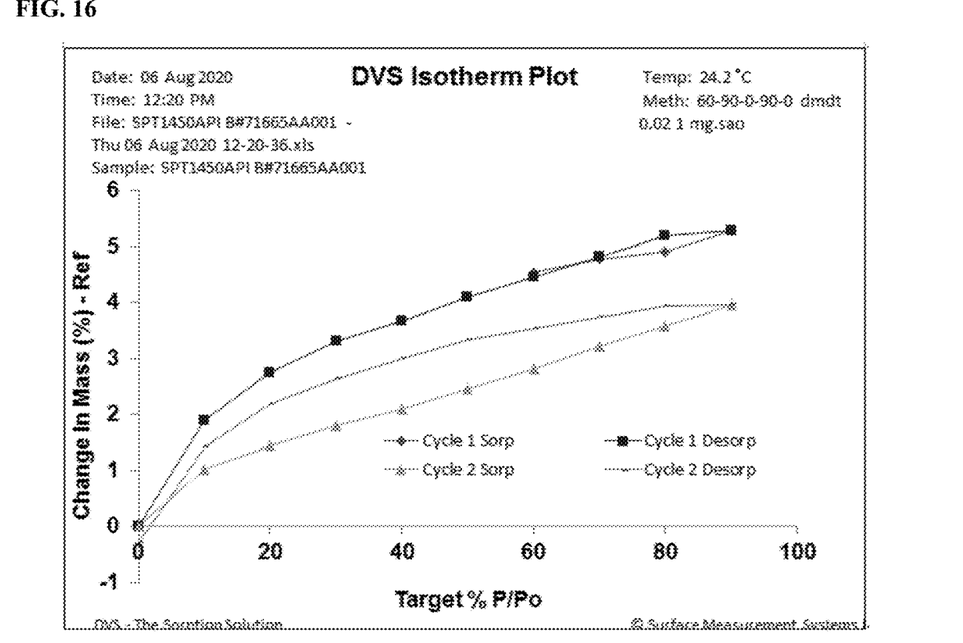
FIG. 16 shows the dynamic vapor sorption (DVS) measurement chart recorded for crystalline form S5 of ivacaftor.

In some embodiments, crystalline form S5 of ivacaftor is characterized by a dynamic vapor sorption (DVS) measurement chart substantially in accordance with FIG. 16.

VI. A Process for Preparing Crystalline Forms of Ivacaftor

In a fourth aspect, the invention provides a process for preparing any one of crystalline forms S2, S3, S4, and S5 of ivacaftor. The process includes:
a) forming a solution including crude ivacaftor and a solvent;
b) adding an anti-solvent to the solution to form a slurry including a precipitate;
c) isolating the precipitate; and
d) drying the precipitate at a temperature of from about 55° C. to about 140° C. to provide crystalline form S2, S3, S4, or S5 of ivacaftor.

In general, the crude ivacaftor used in the methods of the invention can include ivacaftor and at least one other substance associated with the synthesis and/or purification of the ivacaftor (e.g., a solvent; a starting material or intermediate; a reagent such as an acid or base; or a combination thereof). In general, the crude ivacaftor can include in an amount of at least 50% by weight. The crude ivacaftor can include ivacaftor in an amount of, for example, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 99% by weight. The crude ivacaftor can be obtained in a number of forms prior to dissolution according to the methods of the invention. For example, the crude compound can be an amorphous form, a glass, or a foam.

A variety of solvents are suitable for dissolving the crude ivacaftor and can be used for forming the solution in the process of the invention. Examples of suitable solvents include, but are not limited to, an organic solvent miscible with water. In some embodiment, the solvent includes a water-miscible organic solvent and water. In some embodiments, the solvent includes acetone and water. In some embodiments, the solvent is a mixture of acetone and water.

In some embodiments, the solvent is a mixture of acetone and water, wherein water is present in an amount of from about 10% to 15% by volume. In some embodiments, the solvent is a mixture of acetone and water, wherein water is present in an amount of about 10% by volume. In some embodiments, the solvent is a mixture of acetone and water, wherein water is present in an amount of about 15% by volume.

Any amount of solvent suitable for dissolving the crude ivacaftor can be used for forming the solution. In general, the solvent will be used in amounts such that the solution includes ivacaftor in an amount of at least about 5% by weight. The solution can include, for example, the crude ivacaftor in an amount of from about 5% to about 10%, or from about 10% to about 15%, or from about 15% to about 20%, or from about 20% to about 25%, or from about 25% to about 30% by weight. In some embodiments, the solution includes the crude ivacaftor in an amount of from about 5% to about 20% by weight. In some embodiments, the solution includes the crude ivacaftor in an amount of from about 5% to about 15% by weight. In some embodiments, the solution includes the crude ivacaftor in an amount of from about 5% to about 10% by weight.

In some embodiments, the solution includes the crude ivacaftor and a mixture of acetone and water, wherein the crude ivacaftor is present in an amount of from about 5% to about 10% by weight; and water is present in the mixture in an amount of about 10% by volume. In some embodiments, the solution includes the crude ivacaftor and a mixture of acetone and water, wherein the crude ivacaftor is present in an amount of from about 5% to about 10% by weight; and water is present in the mixture in an amount of about 15% by volume.

In some embodiments, forming the solution includes heating the solution. In some embodiments, the solution is heated to a temperature of at least about 40° C. The solution can be heated, for example, at a temperature of from about 40° C. to about 60° C., from about 50° C. to about 60° C., from about 55° C. to about 60° C., or reflux. In some embodiments, forming the solution includes heating the solution including acetone and water to a temperature of from about 40° C. to about 60° C. In some embodiments, forming the solution includes heating the solution including acetone and water to a temperature of from about 50° C. to about 60° C. In some embodiments, forming the solution includes heating the solution including acetone and water to a temperature of from about 55° C. to about 60° C.

One of skill in the art will appreciate that the heating temperature will depend, in part, on one or more factors including the particular solvent (e.g., a mixture of a water-miscible organic solvent and water), the quantity of the solvent, and the level of purity of the crude ivacaftor. Such factors will also determine, to an extent, the length of time required to dissolve the crude compound. Any suitable length of the time can be used, ranging from a few minutes to several hours. For example, the mixture including the crude ivacaftor and the solvent (e.g., acetone and water) can be mixed, with heating, for about 10 minutes, or about 20 minutes, or 30 minutes, or about 40 minutes, or about 1 hour.

In some embodiments, prior to step b), the solution including the crude ivacaftor is further treated with an active carbon. In some embodiments, prior to step b), the solution including the crude ivacaftor and the mixture of acetone and water is further treated with an active carbon at a temperature of from about 40° C. to about 60° C. In some embodiments, prior to step b), the solution including the crude ivacaftor and the mixture of acetone and water is further treated with an active carbon at a temperature of from about 50° C. to about 60° C. In some embodiments, prior to step b), the solution including the crude ivacaftor and the mixture of acetone and water is further treated with an active carbon at a temperature of from about 55° C. to about 60° C. After treatment, the active carbon can be removed by filtration and the resulted solids can be further washed with the solvent to provide a filtrate. In some embodiments, the active carbon is removed by filtration and the solid is further washed with a pre-heated mixture of acetone and water to provide a filtrate.

In general, the filtrate after removing the active carbon is further heated to the original temperature of the solution prior to the addition of the anti-solvent. In some embodiments, the filtrate including the crude ivacaftor, acetone, and water is further heated to a temperature of from about 40° C. to about 60° C. In some embodiments, the filtrate including the crude ivacaftor, acetone, and water is further heated to a temperature of from about 55° C. to about 60° C.

Any liquid substance suitable for precipitating ivacaftor can be used as the anti-solvent in the process for preparing ivacaftor as any one of crystalline forms S2, S3, S4, and S5. In some embodiments, the anti-solvent is water.

In some embodiments, the slurry includes the anti-solvent in an amount of from about 40% to about 70% by weight. In some embodiments, the slurry includes the anti-solvent in an amount of from about 40% to about 60% by weight. In some embodiments, when the solvent includes water and the anti-solvent is water, the slurry includes water in an amount of from about 40% to about 70% by weight. In some embodiments, when the solvent includes water and the anti-solvent is water, the slurry includes water in an amount of from about 50% to about 70% by weight. In some embodiments, when the solvent is a mixture of acetone and water and the anti-solvent is water, the slurry includes water in an amount of from about 40% to about 70% by weight. In some embodiments, when the solvent is a mixture of acetone and water and the anti-solvent is water, the slurry includes water in an amount of from about 50% to about 70% by weight.

In some embodiments, the method further includes cooling the slurry prior to isolating the precipitate. In some embodiments, the slurry is cooled to a temperature of lower than about 30° C.

Isolating the precipitated ivacaftor from the solvent/anti-solvent mixture can be accomplished by a number of techniques, including passing the mixture through a filter to isolate the solid material or centrifuging the mixture and removing the solvent/anti-solvent supernatant. In some embodiments, the process further includes washing the isolated precipitate. Washing can be conducted by triturating the precipitate with additional portions of the anti-solvent (e.g., water) or a solvent/anti-solvent mixture (e.g., acetone and water). The washing can remove residual impurities, if present.

After isolating the precipitated ivacaftor, with or without additional washing steps, the ivacaftor is dried to remove solvent and anti-solvent from the solid material. Drying can be conducted under ambient temperature and pressure. Evaporation of solvent and anti-solvent can be promoted by contacting the solid material with a stream of air, nitrogen, argon, or other another gas or gas mixture. In some embodiments, the precipitate is dried under a reduced pressure. In some embodiments, the precipitate is dried under a reduced pressure and at an elevated temperature. In some embodiments, drying the precipitate includes heating the precipitate to a temperature of from about 55° C. to about 140° C. In some embodiments, drying the precipitate includes heating the precipitate to a temperature of from about 55° C. to about 65° C. to provide crystalline form S3 or S5 of ivacaftor. In some embodiments, drying the precipitate includes heating the precipitate to a temperature of from about 100° C. to about 140° C. to provide crystalline form S2 or S4 of ivacaftor.

A. Embodiments for Preparing Crystalline Form S2 of Ivacaftor

In some embodiments, the present invention provides a process for preparing the crystalline form S2 of ivacaftor. The process includes:
 a) forming a solution comprising crude ivacaftor and a solvent;
 b) adding an anti-solvent to the solution to form a slurry comprising a precipitate;
 c) isolating the precipitate; and
 d) drying the precipitate at a temperature of from about 100° C. to about 140° C. to obtain the crystalline form S2 of Ivacaftor.

With respect to the preparation of crystalline form S2 of Ivacaftor, in some embodiments, the solvent is a mixture of acetone and water; and water is present in the mixture in an amount of about 10% by volume. In some embodiments, in step a), the solution is heated to a temperature of from about 55° C. to 60° C. In some embodiments, the solution is further treated with an active carbon at a temperature of from about 55° C. to 60° C. In some embodiments, the active carbon is removed by filtration; and the solid is washed with a preheated mixture of acetone and water to provide a filtrate. In some embodiments, the filtrate is further heated to a temperature of from about 55° C. to 60° C. prior to the addition of an anti-solvent. In some embodiments, the anti-solvent is water. In some embodiments, drying the precipitate is conducted at a temperature of from about 130° C. to about 140° C.

Embodiment 1: A process for preparing the crystalline form S2 of ivacaftor, the process comprising:
 a) forming a solution comprising crude ivacaftor and a solvent;
 b) adding an anti-solvent to the solution to form a slurry comprising a precipitate;
 c) isolating the precipitate; and d) drying the precipitate at a temperature of from about 100° C. to about 140° C. to obtain the crystalline form S2 of Ivacaftor.

Embodiment 2: The process of embodiment 1, wherein the solvent comprises a water-miscible organic solvent and water.

Embodiment 3: The process of embodiment 1 or 2, wherein the solvent is a mixture of acetone and water.

Embodiment 4: The process of embodiment 3, wherein water is present in the mixture in an amount of about 10% by volume.

Embodiment 5: The process of any one of embodiments 1-4, wherein forming the solution comprises heating the solution.

Embodiments 6: The process of embodiment 5, wherein the solution is heated to a temperature of from about 40° C. to about 60° C., from about 50° C. to about 60° C., or from about 55° C. to about 60° C.

Embodiment 7: The process of embodiment 5 or 6, wherein the solution is heated to a temperature of from about 55° C. to about 60° C.

Embodiment 8: The process of any one of embodiments 1 to 7, prior to step b), the solution is optionally treated with an active carbon.

Embodiment 9: The process of embodiment 8, wherein treating with an active carbon is conducted at a temperature of from about 40° C. to about 60° C., from about 50° C. to about 60° C., or from about 55° C. to about 60° C.

Embodiment 10: The process of embodiment 8 or 9, wherein treating with an active carbon is conducted at a temperature of from about 55° C. to about 60° C.

Embodiment 11: The process of embodiment 10, wherein the active carbon is removed by filtration to provide a filtrate.

Embodiment 12: The process of embodiment 11, wherein the filtrate is further heated to a temperature of from about 40° C. to about 60° C., from about 50° C. to about 60° C., or from about 55° C. to about 60° C., prior to the addition of the anti-solvent.

Embodiment 13: The process of embodiment 11 or 12, wherein the filtrate is further heated to a temperature of from about 55° C. to about 60° C., prior to the addition of the anti-solvent.

Embodiment 14: The process of any one of embodiments 1 to 13, wherein the anti-solvent is water.

Embodiment 15: The process of any one of embodiments 1 to 14, further comprising cooling the slurry prior to isolating the precipitate.

Embodiment 16: The process of embodiment 15, wherein the slurry is cooled to a temperature of lower than about 30° C.

Embodiment 17: The process of any one of embodiments 1 to 16, wherein the solution comprises the crude ivacaftor in an amount of from about 5% to about 30% by weight.

Embodiment 18: The process of any one of embodiments 1 to 17, wherein the slurry comprises the anti-solvent in an amount of from about 40% to about 70% by weight.

Embodiment 19: The process of any one of embodiments 1 to 18, wherein drying the precipitate comprises heating the precipitate to a temperature of from about 130° C. to about 140° C.

Embodiment 20: The process of any one of embodiments 1 to 19, further comprising washing the precipitate prior to drying the precipitate.

B. Embodiments for Preparing Crystalline Form S5 of Ivacaftor

In some embodiments, the present invention provides a process for preparing the crystalline form S5 of ivacaftor. The process includes:
a) forming a solution comprising crude ivacaftor and a solvent;
b) adding an anti-solvent to the solution to form a slurry comprising a precipitate;
c) isolating the precipitate; and
d) drying the precipitate at a temperature of from about 55° C. to about 65° C. to obtain the crystalline form S5 of ivacaftor.

With respect to the preparation of crystalline form S5 of Ivacaftor, in some embodiments, the solvent is a mixture of acetone and water; and water is present in the mixture in an amount of about 15% by volume. In some embodiments, in step a), the solution is heated to a temperature of from about 40° C. to 60° C. In some embodiments, the solution is further treated with active carbon at a temperature of from about 40° C. to 60° C. In some embodiments, the active carbon is removed by filtration; and the solid is washed with a preheated mixture of acetone and water to provide a filtrate. In some embodiments, the filtrate is further heated to a temperature of from about 40° C. to 60° C. prior to the addition of an anti-solvent. In some embodiments, the anti-solvent is water.

Embodiment 1: A process for preparing the crystalline form S5 of ivacaftor, the process comprising:
a) forming a solution comprising crude ivacaftor and a solvent;
b) adding an anti-solvent to the solution to form a slurry comprising a precipitate;
c) isolating the precipitate; and
d) drying the precipitate at a temperature of from about 55° C. to about 65° C. to obtain the crystalline form S5 of Ivacaftor.

Embodiment 2: The process of embodiment 1, wherein the solvent comprises a water-miscible organic solvent and water.

Embodiment 3: The process of embodiment 1 or 2, wherein the solvent is a mixture of acetone and water.

Embodiment 4: The process of embodiment 3, wherein water is present in the mixture in an amount of about 15% by volume.

Embodiment 5: The process of any one of embodiments 1-4, wherein forming the solution comprises heating the solution.

Embodiments 6: The process of embodiment 5, wherein the solution is heated to a temperature of from about 40° C. to about 60° C.

Embodiment 7: The process of any one of embodiments 1 to 6, prior to step b), the solution is optionally treated with an active carbon.

Embodiment 8: The process of embodiment 7, wherein treating with an active carbon is conducted at a temperature of from about 40° C. to about 60° C.

Embodiment 9: The process of embodiment 8, wherein the active carbon is removed by filtration to provide a filtrate.

Embodiment 10: The process of embodiment 9, wherein the filtrate is further heated to a temperature of from about 40° C. to about 60° C., prior to the addition of the anti-solvent.

Embodiment 11: The process of any one of embodiments 1 to 10, wherein the anti-solvent is water.

Embodiment 12: The process of any one of embodiments 1 to 11, further comprising cooling the slurry prior to isolating the precipitate.

Embodiment 13: The process of embodiment 12, wherein the slurry is cooled to a temperature of lower than about 30° C.

Embodiment 14: The process of any one of embodiments 1 to 13, wherein the solution comprises the crude ivacaftor in an amount of from about 5% to about 30% by weight.

Embodiment 15: The process of any one of embodiments 1 to 14, wherein the slurry comprises the anti-solvent in an amount of from about 40% to about 70% by weight.

Embodiment 16: The process of any one of embodiments 1 to 15, further comprising washing the precipitate prior to drying the precipitate.

VII. Examples

The following examples describe a novel crystalline forms of ivacaftor and processes suitable for its preparation on a laboratory-scale or an industrial scale. The present invention includes, but is not limited to, the embodiments described in the examples.

Example 1: Methods for Characterizing Solid Forms of Ivacaftor

X-RAY POWDER DIFFRACTION. Powder X-ray Diffraction patterns were collected on a Bruker AXS D8 diffractometer using Cu Kα1 radiation (40 kV, 40 mA), 0-20 goniometer, a Ge monochromator and LynxEye detector. XRPD patterns were collected under ambient condition. The scanning parameters included an angular range of 2-40°, a step size of 0.02°, and a scan speed of 0.6 sec/step.

THERMAL GRAVIMETRIC ANALYSIS (TGA). TGA data was collected on a TA Instrument Q500 TGA. Each sample (15-20 mg) was loaded onto a pre-tared platinum crucible and the balance and furnace were purged with nitrogen prior to the analysis with a flow rate set as 40±5 and 60±5 mL/min, respectively. The heating process was programmed to start at the ambient temperature and stop at 300° C. with a 10° C./min ramp.

DIFFERENTIAL SCANNING CALORIMETRY (DSC). DSC data was collected on a TA Instrument MDSC Q200. Each sample (1-5 mg) was loaded onto a T-zero hermetic pan with a pin-hole lid and the analysis was carried out under a constant flow of nitrogen (60 mL/min). The heating process was programmed to start from 30° C. and stop at 350° C. with a 10° C./min ramp.

DYNAMIC VAPOR SORPTION (DVS). The sample was placed into the DVS sample pan and the initial relative humidity was set as 60% RH. The moisture was gradually introduced into the system with a 10% RH increment up to 90% RH and the humidity was then decreased in a similar trend for desorption phase. The sorption and desorption data were collected with equilibration set to dm/dt 0.001%/min for 5 min/step. The minimum and maximum time for each step were set to 10 and 360 min. Two or three sorption/desorption cycles were performed.

Figure 5:
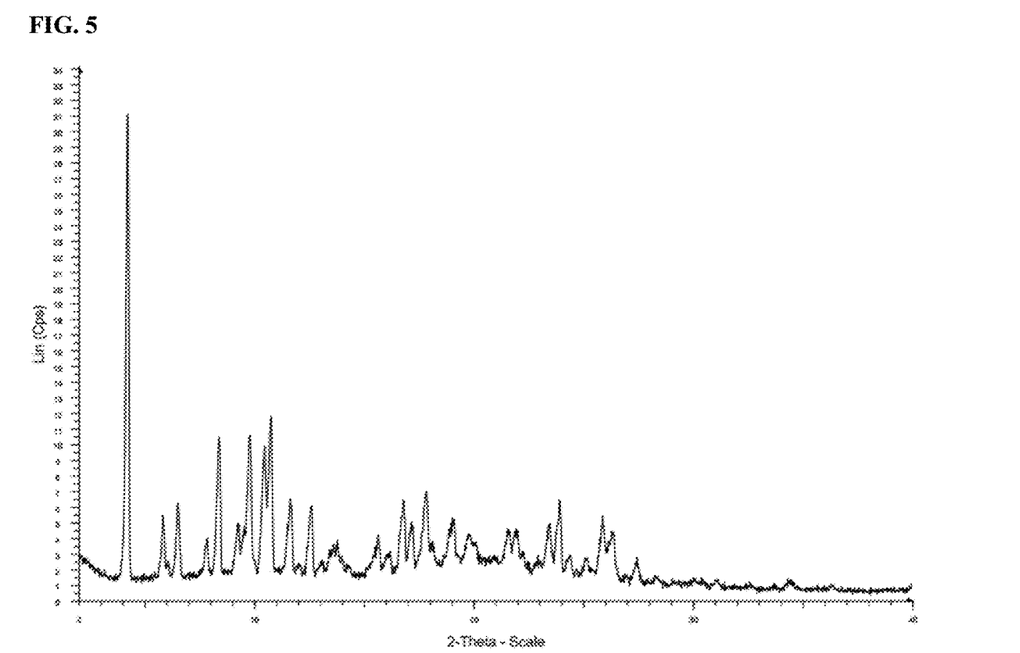
FIG. 5 shows the X-ray powder diffraction (XRPD) pattern recorded for crystalline form S3 of ivacaftor.
Figure 6:
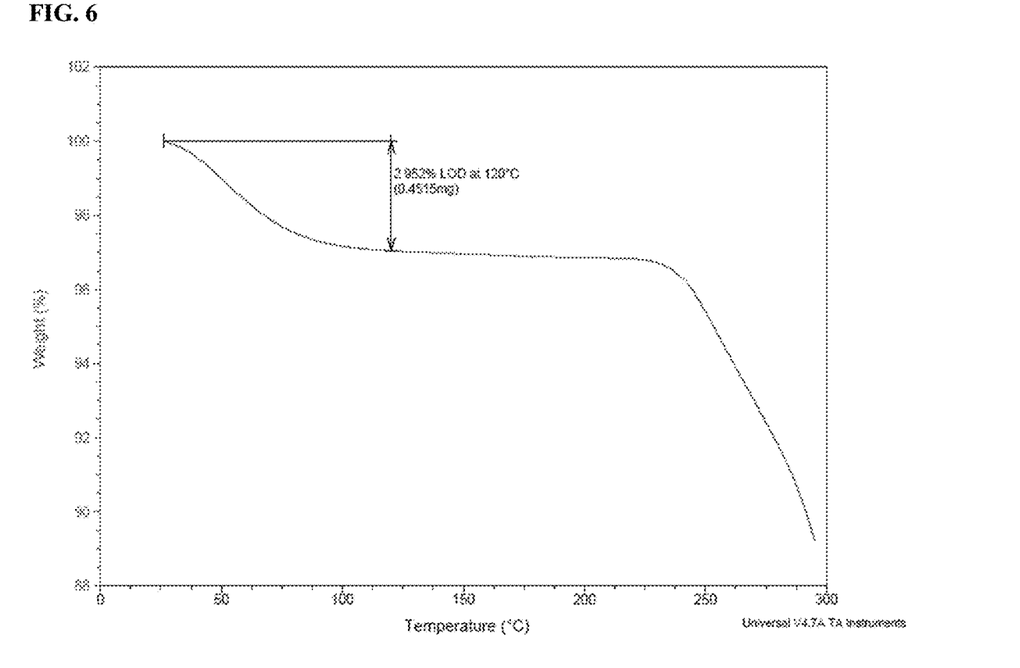
FIG. 6 shows the thermogravimetric analysis (TGA) thermogram recorded for crystalline form S3 of ivacaftor
Figure 7:
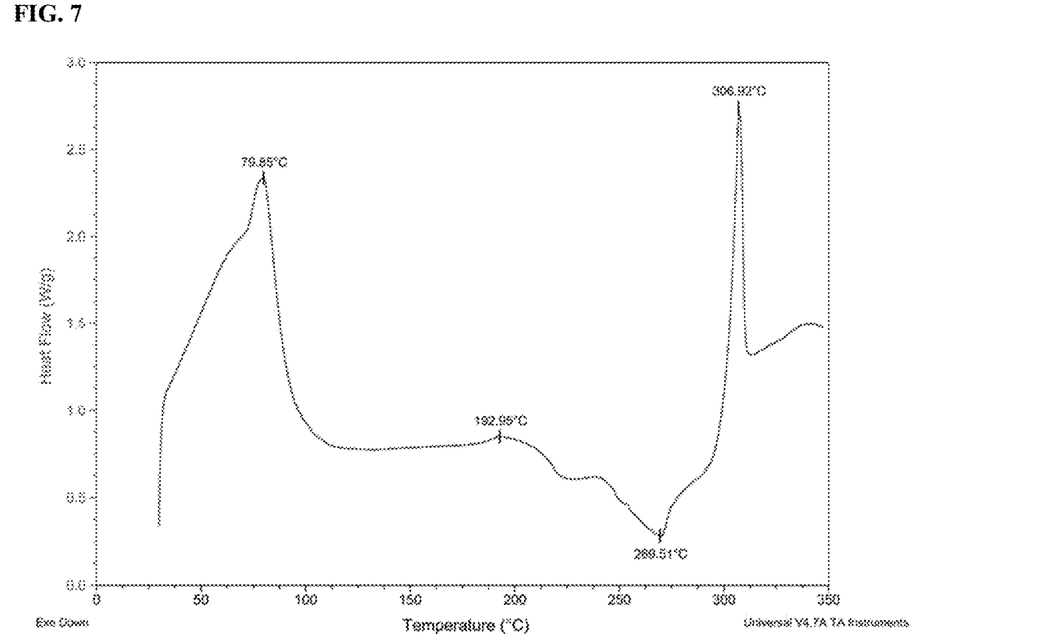
FIG. 7 shows the differential scanning calorimetry (DSC) thermogram recorded for crystalline form S3 of ivacaftor
Figure 8:
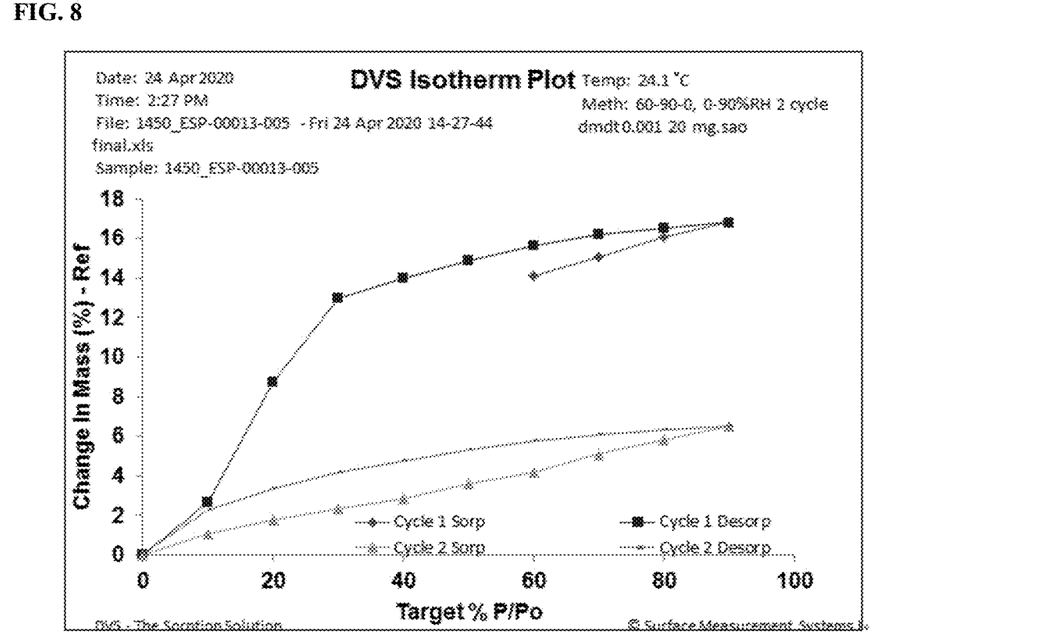
FIG. 8 shows the dynamic vapor sorption (DVS) measurement chart recorded for crystalline form S3 of ivacaftor.

Example 2: Preparation of Crystalline Form S2 and S3 of Ivacaftor 1.658 kg of Ivacaftor was added to 13.46 kg of 10% water in acetone at room temperature, heating to 55-59° C. (reflux) . 0.083 kg active carbon was added at about 58° C. The resulting suspension was filtered and the solid was washed with 2.69 kg of pre-hot 10% water in acetone to obtain a filtrate. The filtrate was heated to about 59° C. 18.24 kg of water was added at about 57° C. then cooled to 20-30° C. The resulting suspension was filtered and the solid was dried at 55-65° C. for 8 hours to provide the crystalline form S3 (Table 3, FIG. 5) of Ivacaftor and then dried at 130-140° C. for about 16 hours to provide the crystalline form S2 (Table 2, FIG. 1) of Ivacaftor.

The PXRD data of S2 and S3 forms are summarized below in Table 2 and Table 3, respectively.

TABLE 2

PXRD peak data for ivacaftor crystalline Form S2

| Angle (2θ) | Intensity (Cps) | Intensity (%) |
|---|---|---|
| 4.119 | 21.435 | 100 |
| 8.217 | 10.751 | 27.5 |
| 9.268 | 9.535 | 25.5 |
| 9.941 | 8.891 | 31.7 |
| 10.404 | 8.496 | 34.4 |
| 11.714 | 7.549 | 35.4 |
| 16.402 | 5.4 | 34.3 |
| 17.408 | 5.09 | 34.3 |

TABLE 3

PXRD peak data for ivacaftor crystalline Form S3

| Angle (2θ) | Intensity (Cps) | Intensity (%) |
|---|---|---|
| 4.158 | 21.232 | 100 |
| 5.781 | 15.275 | 17.5 |
| 6.468 | 13.654 | 20.1 |
| 7.769 | 11.37 | 12.8 |
| 8.326 | 10.611 | 33.6 |
| 9.209 | 9.595 | 16.1 |
| 9.735 | 9.078 | 34 |
| 10.412 | 8.489 | 31.7 |
| 10.7 | 8.261 | 37.5 |
| 11.612 | 7.614 | 21 |
| 12.01 | 7.363 | 7.6 |
| 12.531 | 7.058 | 19.2 |
| 13.03 | 6.789 | 8.3 |
| 13.568 | 6.521 | 11.5 |
| 13.746 | 6.437 | 12.4 |
| 14.257 | 6.208 | 7.4 |
| 15.615 | 5.671 | 13.6 |
| 16.113 | 5.496 | 9.6 |
| 16.762 | 5.285 | 20.4 |
| 17.14 | 5.169 | 16.2 |
| 17.792 | 4.981 | 21.8 |
| 18.099 | 4.897 | 12.2 |
| 19.029 | 4.66 | 17 |
| 19.757 | 4.49 | 13.6 |
| 20.027 | 4.43 | 12.1 |
| 21.585 | 4.114 | 14.5 |
| 21.921 | 4.051 | 14.8 |
| 22.215 | 3.998 | 10.2 |
| 22.955 | 3.871 | 8.4 |
| 23.422 | 3.795 | 15.8 |
| 23.898 | 3.721 | 20.6 |
| 24.363 | 3.651 | 9.3 |
| 25.129 | 3.541 | 8.8 |
| 25.867 | 3.442 | 17.4 |
| 26.328 | 3.382 | 14.1 |
| 27.43 | 3.249 | 8.9 |
| 28.324 | 3.148 | 5 |
| 31.077 | 2.875 | 4.3 |
| 33.721 | 2.656 | 3 |
| 34.435 | 2.602 | 4.3 |
| 34.533 | 2.595 | 4.3 |
| 36.337 | 2.47 | 3.2 |

Example 3: Preparation of Crystalline Form S3 of Ivacaftor 10 g of Ivacaftor was added to 100 mL of 10% water in acetone at room temperature, heating to 55-59° C. (reflux). 0.5 g active carbon was added at about 58° C. The resulting suspension was filtered and the solid was washed with 20 mL of pre-hot 10% water in acetone to obtain a filtrate. The filtrate was heated to about 59° C. 0.1 g of seed was added at 50-60° C. and hold for 30 minutes. 110 mL of water was added at 50-60° C. then cooled to 2030° C. The resulting suspension was filtered and the solid was dried at 55-65° C. for about 20 hours to provide the crystalline form S3 of Ivacaftor. The PXRD pattern of the dried ivacaftor was recorded, which was substantially identical to the pattern illustrated in FIG. 5.

Example 4: Preparation of Crystalline Forms S2 and S4 of Ivacaftor 1-2 g crystalline form S3 of Ivacaftor was dried at 115-125° C. for 2 hours to provide the crystalline form S2 of Ivacaftor; then dried at 115-125° C. for additional 2.5 hours to provide the crystalline form S4. See Table 4 of Ivacaftor. The PXRD pattern of the first dried ivacaftor was recorded, which was substantially identical to the pattern illustrated in FIG. 1 (S2 form). The PXRD pattern of further dried ivacaftor was recorded, which was substantially identical to the pattern illustrated in FIG. 9 (S4 form).

TABLE 4

PXRD peak data for ivacaftor crystalline Form S4

| Angle (2θ) | Intensity (Cps) | Intensity (%) |
|---|---|---|
| 4.259 | 20.729 | 100 |

Example 5: Preparation of Crystalline Form S5 of Ivacaftor 6.279 kg of Ivacaftor was added to 81.90 kg of 15% water in acetone at room temperature, heating to 40-60° C. 0.3 kg active carbon was added at 40-60° C. The resulting suspension was filtered and the solid was washed with 5.10 kg of pre-hot 15% water in acetone to obtain a filtrate. The filtrate was heated to 40-60° C. 69.10 kg of water was added at 40-60° C. then cooled to 20-30° C. The resulting suspension was filtered and the solid was dried at 55-65° C. for 33-46 hours to provide the crystalline form S5 of Ivacaftor. The PXRD pattern of the dried ivacaftor was recorded, which was substantially identical to the pattern illustrated in FIG. 13. The PXRD data is summarized in below in Table 5.

TABLE 5

PXRD peak data for ivacaftor crystalline Form S5

| Angle (2θ) | Intensity (Cps) | Intensity (%) |
|---|---|---|
| 4.253 | 20.76 | 100 |
| 4.611 | 19.148 | 55 |
| 10.011 | 8.828 | 47.6 |
| 18.327 | 4.837 | 36.5 |
| 18.75 | 4.729 | 35.9 |
| 16.769 | 5.283 | 34.2 |
| 20.042 | 4.427 | 33 |
| 12.707 | 6.961 | 31.5 |
| 13.891 | 6.37 | 31.3 |
| 15.283 | 5.793 | 30.8 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. Crystalline form S2 of ivacaftor, characterized by an X-ray powder diffraction pattern comprising three or more peaks at 4.1, 8.2, 9.3, 9.9, 10.4, 11.7, 16.4 and 17.4 degrees 2θ (±0.2 degrees 2θ).

2. The crystalline form S2 of ivacaftor according to claim 1, characterized by an X-ray powder diffraction pattern comprising five or more peaks at 4.1, 8.2, 9.3, 9.9, 10.4, 11.7, 16.4 and 17.4 degrees 2θ (±0.2 degrees 2θ).

3. The crystalline form S2 of ivacaftor according to claim 1, wherein the X-ray powder diffraction pattern is substantially in accordance with FIG. 1.

4. The crystalline form S2 of ivacaftor according to claim 1, further characterized by a weight loss of about 3.0% upon heating to about 120° C., as measured by a thermal gravimetric analysis.

5. The crystalline form S2 of ivacaftor according to claim 4, wherein the thermal gravimetric analysis is substantially in accordance with FIG. 2.

6. The crystalline form S2 of ivacaftor according to claim 1, further characterized by a differential scanning calorimetry thermogram comprising three endothermic peaks at about 64° C., 192° C. and 303° C.; and one exothermic peak at about 253° C.

7. The crystalline form S2 of ivacaftor according to claim 6, further characterized by a differential scanning calorimetry thermogram substantially in accordance with FIG. 3.

8. A process for preparing the crystalline form S2 of ivacaftor of claim 1, the process comprising:
   a) forming a solution comprising crude ivacaftor and a solvent;
   b) adding an anti-solvent to the solution to form a slurry comprising a precipitate;
   c) isolating the precipitate; and
   d) drying the precipitate at a temperature of from about 100° C. to about 140° C. to provide the crystalline form S2 of Ivacaftor.

9. The process of claim 8, wherein the solvent is a mixture of acetone and water; water is present in the mixture in an amount of about 10% by volume; and the anti-solvent is water.

10. Crystalline form S5 of ivacaftor, characterized by an X-ray powder diffraction pattern comprising three or more peaks at 4.3, 4.6, 10.0, 12.7, 13.9, 15.3, 16.8, 18.3, 18.8, and 20.0 degrees 2θ (±0.2 degrees 2θ).

11. The crystalline form S5 of ivacaftor according to claim 10, characterized by an X-ray powder diffraction pattern comprising five or more peaks at 4.3, 4.6, 10.0, 12.7, 13.9, 15.3, 16.8, 18.3, 18.8, and 20.0 degrees 2θ (±0.2 degrees 2θ).

12. The crystalline form S5 of ivacaftor according to claim 10, wherein the X-ray powder diffraction pattern is substantially in accordance with FIG. 13.

13. The crystalline form S5 of ivacaftor according to claim 10, further characterized by a weight loss of from about 3% to about 4% upon heating to about 200° C., as measured by a thermal gravimetric analysis.

14. The crystalline form S5 of ivacaftor according to claim 13, wherein the thermal gravimetric analysis is substantially in accordance with FIG. 14.

15. The crystalline form S5 of ivacaftor according to claim 10, further characterized by a differential scanning calorimetry thermogram comprising two endothermic peaks at about 198° C. and 302° C. and one exothermic peak at about 226° C.

16. The crystalline form S5 of ivacaftor according to claim 15, further characterized by a differential scanning calorimetry thermogram substantially in accordance with FIG. 15.

17. A process for preparing the crystalline form S5 of ivacaftor of claim 10, the process comprising:
  a) forming a solution comprising crude ivacaftor and a solvent;
  b) adding an anti-solvent to the solution to form a slurry comprising a precipitate;
  c) isolating the precipitate; and
  d) drying the precipitate at a temperature of from about 55° C. to about 65° C. to provide the crystalline form S5 of ivacaftor.

18. The process of claim 17, wherein the solvent is a mixture of acetone and water.

19. The process of claim 18, wherein water is present in the mixture in an amount of about 15% by volume.

20. The process of claim 17, wherein the anti-solvent is water.

* * * * *